(12) United States Patent
Annis

(10) Patent No.: US 7,860,211 B1
(45) Date of Patent: Dec. 28, 2010

(54) METHOD OF PRODUCING A LAMINOGRAPHY IMAGE WITH A ROTATING OBJECT, FIXED X-RAY SOURCE, AND FIXED DETECTOR COLUMNS

(76) Inventor: Martin Annis, 65 Banks St., Cambridge, MA (US) 02138

( * ) Notice: Subject to any disclaimer, the term of this patent is extended or adjusted under 35 U.S.C. 154(b) by 0 days.

(21) Appl. No.: 12/825,245

(22) Filed: Jun. 28, 2010

Related U.S. Application Data

(60) Provisional application No. 61/269,540, filed on Jun. 26, 2009, provisional application No. 61/275,667, filed on Sep. 2, 2009.

(51) Int. Cl.
*A61B 6/00* (2006.01)
(52) U.S. Cl. .......................... 378/21; 378/57
(58) Field of Classification Search .................. 378/21, 378/57
See application file for complete search history.

(56) References Cited

U.S. PATENT DOCUMENTS

| | | | |
|---|---|---|---|
| 6,584,170 B2 | 6/2003 | Aust et al. | |
| 6,898,266 B2 * | 5/2005 | Griffith | 378/22 |
| 6,960,020 B2 * | 11/2005 | Lai | 378/207 |
| 6,977,985 B2 * | 12/2005 | Bohn et al. | 378/27 |
| 7,012,987 B1 | 3/2006 | Annis | |
| 7,221,732 B1 * | 5/2007 | Annis | 378/57 |
| 7,672,427 B2 * | 3/2010 | Chen et al. | 378/57 |

* cited by examiner

*Primary Examiner* — Edward J Glick
*Assistant Examiner* — Alexander H Taningco
(74) *Attorney, Agent, or Firm* — Altman & Martin; Steven K. Martin

(57) ABSTRACT

A method of producing a laminography image of an object. The object is rotated on a platform in an object space between a fixed x-ray source and multiple columns of detector elements. Two samples of each voxel are taken at each detector column, one for each of the two alignments of the x-ray source, voxel, and detector column as the object rotates. It is generally possible to image the entire object in one rotation. Optionally, the platform axis can be offset from the system center line or the platform can be translated through the object space in the plane of the platform in order to make sure that each voxel traverses all of the detector columns to acquire maximum data. Once all of the data for all of the voxels is acquired, it is used with any appropriate laminography algorithm to produce images of the object.

6 Claims, 5 Drawing Sheets

METHOD OF PRODUCING A LAMINOGRAPHY IMAGE WITH A ROTATING OBJECT, FIXED X-RAY SOURCE, AND FIXED DETECTOR COLUMNS

CROSS-REFERENCES TO RELATED APPLICATIONS

The applicant wishes to claim the benefit of U.S. Provisional Patent Application No. 61/269,540, filed Jun. 26, 2009 for 3RD GENERATION CT SYSTEM WITH FIXED X-RAY SOURCE AND FIXED ROWS OF DETECTORS in the name of Martin Annis and of U.S. Provisional Patent Application No. 61/275,667, filed Sep. 2, 2009 for LAMINOGRAPHY SYSTEM WITH A ROTATING OBJECT, A FIXED X-RAY SOURCE AND FIXED ROWS OF DETECTORS in the name of Martin Annis.

STATEMENT REGARDING FEDERALLY SPONSORED RESEARCH OR DEVELOPMENT

Not Applicable

REFERENCE TO A SEQUENCE LISTING, A TABLE, OR A COMPUTER PROGRAM LISTING COMPACT DISK APPENDIX

Not Applicable

BACKGROUND OF THE INVENTION

1. Field of the Invention

The present invention relates to x-ray imaging, more particularly, to methods of producing laminography x-ray images.

2. Description of the Related Art

X-ray laminography is the process by which a flat plane (or, more recently, a single voxel) inside an object can be sharply imaged while all other planes inside the object are blurred. Laminography systems have existed for many decades. The original laminography x-ray systems were used to diagnose cancer in the lungs. The patient would lie on his back on a gantry with an x-ray film below him and an x-ray source above him. The source and the film were then moved simultaneously in a manner such that only one horizontal plane remained in focus, with all other planes being blurred. The process was then repeated to focus another plane.

In recent years, digital radiography has allowed the focusing of each of the planes simultaneously. However the introduction of computed tomography (CT) has replaced the use of laminography in most medical applications. One exception is breast imaging, where it is now rapidly being introduced. These systems typically have an x-ray source emitting a cone of x-rays above the breast and a two-dimensional (2D) detector array below the breast. The patient's breast and the 2D detector remain fixed while the x-ray source moves along an arc above the detector. The x-rays impinge on the detector successively through several angles to the normal to the detector from approximately +/−30°. The reason for not using larger angles is the difficulty of arranging the components of the system around the patient. The data is reduced typically using a complex array of electronics and successive approximations of a maximum likelihood algorithm.

CT, however, has not replaced the majority of conventional transmission x-ray inspection machines in airports and other applications. This is mainly because of the high cost of the CT technology and also the weight and size of the systems.

There is a major difference between CT imaging and laminography imaging. Present day CT technology requires that the x-rays penetrate each voxel in the object from at least 180°, and preferably 360°, within a single flat plane, producing a single slice image. The process is then repeated for each plane to image the entire object. Laminography imaging does not have this limitation. It merely requires that all of the x-rays that traverse a chosen voxel in the object are collected from as many angles as possible (in three dimensions) and that only this data is used to determine the image of this voxel. This procedure is repeated to image every voxel in the object.

Laminography imaging is improved substantially by using a greater number of angles from a larger number of directions in three dimensions. A paucity of angles and the inability to produce views of the voxel from angles that differ greatly from one another are the principal factors in causing streaks and other problems in laminography images.

BRIEF SUMMARY OF THE INVENTION

An object of the present invention is to provide a method of more efficiently collecting data required for a laminography image.

Another object is to provide data for each voxel of an object from many angles, thereby minimizing the artifacts evident in systems of the prior art.

The present invention operates on a system wherein the object being imaged is placed on an x-ray translucent, rotatable platform in an object space. The rotatable platform resides between a fixed x-ray source and multiple columns of detector elements that are preferably arranged as a small arc around the x-ray source. The present invention acquires a large amount of data for every object voxel by rotating the object continuously between the x-ray source and the detector.

The present invention has the unique characteristic that each detector column "sees" each voxel twice as the platform rotates. The second view is from a completely different angle in three dimensions than the first view, thereby doubling the amount of data for each voxel without increasing the number of detector columns. To make sure the second view is different from the first view, the object is displaced from the center of the platform so that there are no voxels on the platform axis of rotation.

The procedure of the present invention is to take a sample of each voxel at each detector column that the voxel traverses for both alignments of the x-ray source, voxel, and detector column as the object rotates. With today's technology, it is generally possible to image the entire object in one rotation.

In some situations, the voxels nearest the platform axis will not traverse one or more outer detector columns. The present invention contemplates two solutions. In the first, the rotating platform axis is offset from the system center line. In another, the rotating platform is translated through the object space in the plane of the platform.

Once all of the data for all of the voxels is acquired, it is used with any appropriate laminography algorithm to produce images of the object.

Application of the present invention include the inspection of airplane carryon bags and the inspection of shipping pallets.

Other objects of the present invention will become apparent in light of the following drawings and detailed description of the invention.

BRIEF DESCRIPTION OF THE DRAWINGS

For a fuller understanding of the nature and object of the present invention, reference is made to the accompanying drawings, wherein.

DETAILED DESCRIPTION OF THE INVENTION

Figure 1:
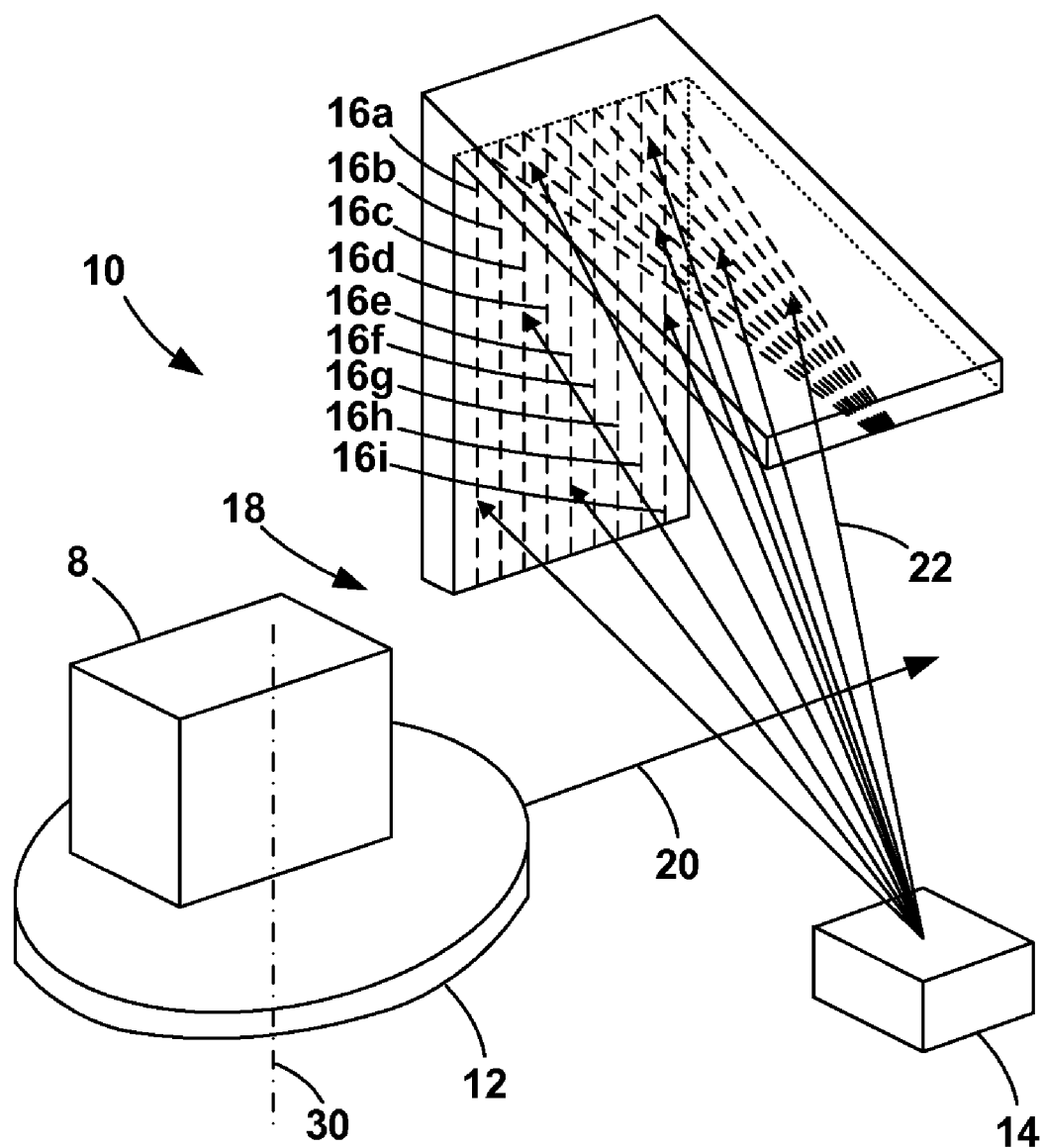
FIG. 1 is a basic perspective diagram of the system with which the present invention is used.
Figure 2:
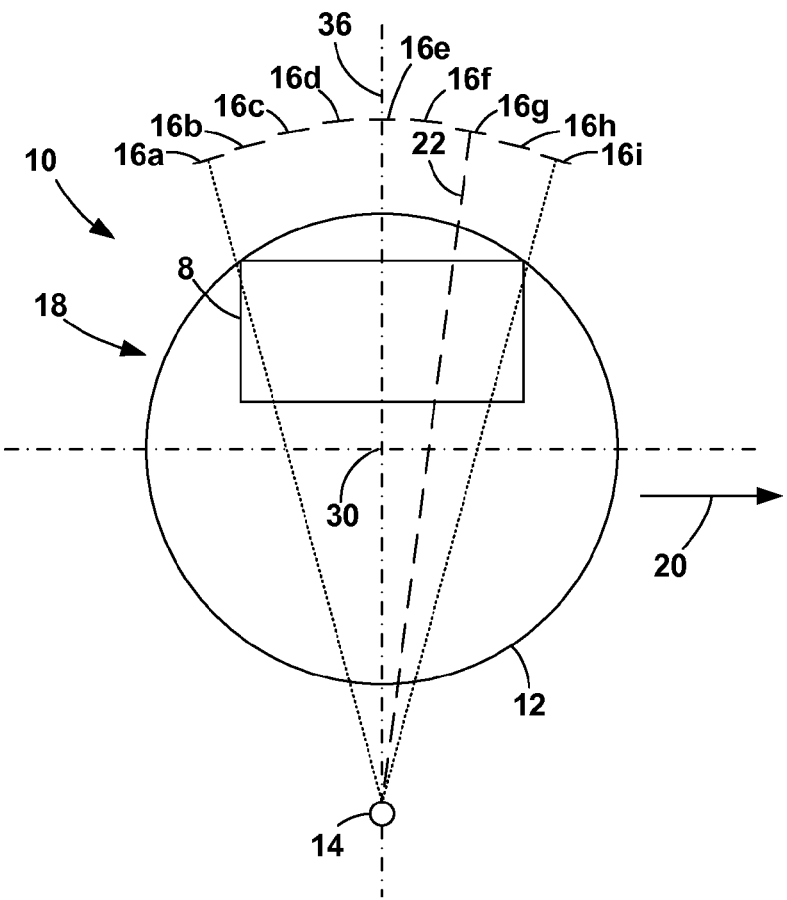
FIG. 2 is a top view of the system of FIG. 1.
Figure 3:
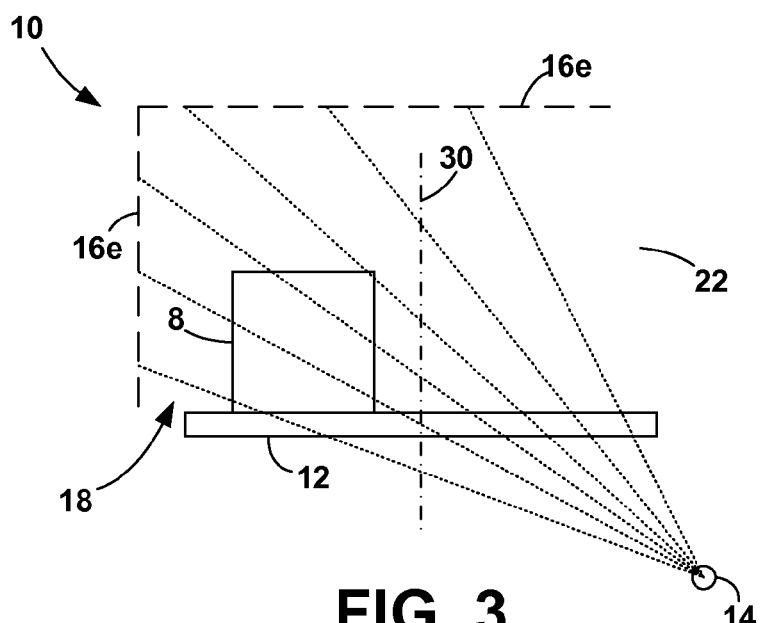
FIG. 3 is a side view of the system of FIG. 1.

A basic diagram of the hardware 10 on which the method of the present invention operates is shown in FIGS. 1-3 and is based on the disclosure of U.S. Pat. No. 6,584,170, issued to Aust et al. That patent discloses a system wherein the object being imaged 8 is placed on an x-ray translucent, rotatable platform 12 in an object space 18. The platform 12 is moved transversely, as at 20, between a fixed x-ray source 14 and a single column 16e of detector elements 34, producing a transmission image. The platform 12 is then rotated by a suitable angle and the process is repeated to produce another transmission image, and so forth. The different images are used to see the object 8 in different two-dimensional views. U.S. Pat. No. 6,584,170 is incorporated herein by reference.

The present invention increases the number of detector columns 16a-16i (collectively, 16), as in FIG. 1, over the single detector column of Aust et al. In the example of FIG. 1, there are nine detector columns, but the present invention contemplates that any number greater the one may be used. Preferably, the detector columns 16 are arranged in a small arc around the x-ray source 14 on the opposite side of the platform 12.

There are a number of different methods of producing laminography images of an object. One such algorithm is disclosed in U.S. Pat. No. 7,012,987 issued to the present applicant. The patent discloses an algorithm that erases much of the blurring in conventional laminography images. The algorithm can be applied very early in the data reduction process, rapidly and at low cost. The algorithm is much simpler than the maximum likelihood algorithm and is based on the physics of the object rather than complex mathematics.

One requirement that all laminography algorithms have in common is the need for data from multiple views of each voxel in the object being imaged. The multiple views must be from different angles in three dimensions.

The present invention achieves a large number of x-ray beam angles through every voxel 32 in the object 8 by rotating the object 8 continuously between the stationary x-ray source 14 and the stationary columns 16 of detector elements 34. Thus, a single rotation of the object 8 through 360° is generally sufficient to collect all of the necessary data. Assuming that the platform axis 30 is stationary relative to the x-ray source 14 and detector columns 16, at each instant of time during the process, the position of every voxel 32 relative to the x-ray source 14 and to every detector column 16 is known by measuring the rotation angle of the platform 12. Also, at each instant of time, many voxels 32 are traversed by several angles of the x-rays beams 22.

The present invention has the unique characteristic that each detector column 16 "sees" the chosen voxel 34 twice as the platform 12 rotates. The second view is from a completely different angle in three dimensions than the first view. Thus, the number of views is doubled without increasing the number of detector columns 16.

In order to make sure that the second view is from a different angle than the first view, the object 8 is displaced from the center of the platform 12 so that the object 8 is not on the platform's axis of rotation 30. If the object 8 is on the axis, the two views of a voxel 32 on the axis 30 will not from different angles and will thus be identical.

The basic procedure of the present invention is to take a sample of each voxel 32 at each detector column 16 that the voxel 32 traverses—passes between the detector column 16 and the x-ray source 14—for both alignments of the x-ray source 14, voxel 32, and detector column 16 as the object 8 rotates.

More specifically, a voxel 32 and a detector column 16 are chosen. As the object 8 rotates, the chosen voxel 32 becomes aligned with the x-ray source 14 and the chosen detector column 16. At this time, the appropriate detector element 34 in the chosen detector column 16 is determined and sampled, giving the first data sample. As the platform continues to rotate, the chosen voxel 32 reaches its next alignment between the x-ray source 14 and the chosen detector column 16. Then the appropriate detector element 34 in the chosen detector column 16 is determined and sampled, giving the second data sample.

This process is performed for the chosen voxel 32 for all of the detector columns 16 that the chosen voxel 32 traverses, which is repeated for all of the voxels 32 of the object 8. With the speed of today's technology and the relatively slow rotation of the platform 12, it is not necessary to rotate the platform 12 for each voxel 32 and each detector column 16. It is generally possible to image the entire object 8 in one rotation, that is, all of the voxels 32 are sampled for all of the detector columns 16 during one rotation of the platform 12.

Figure 4:
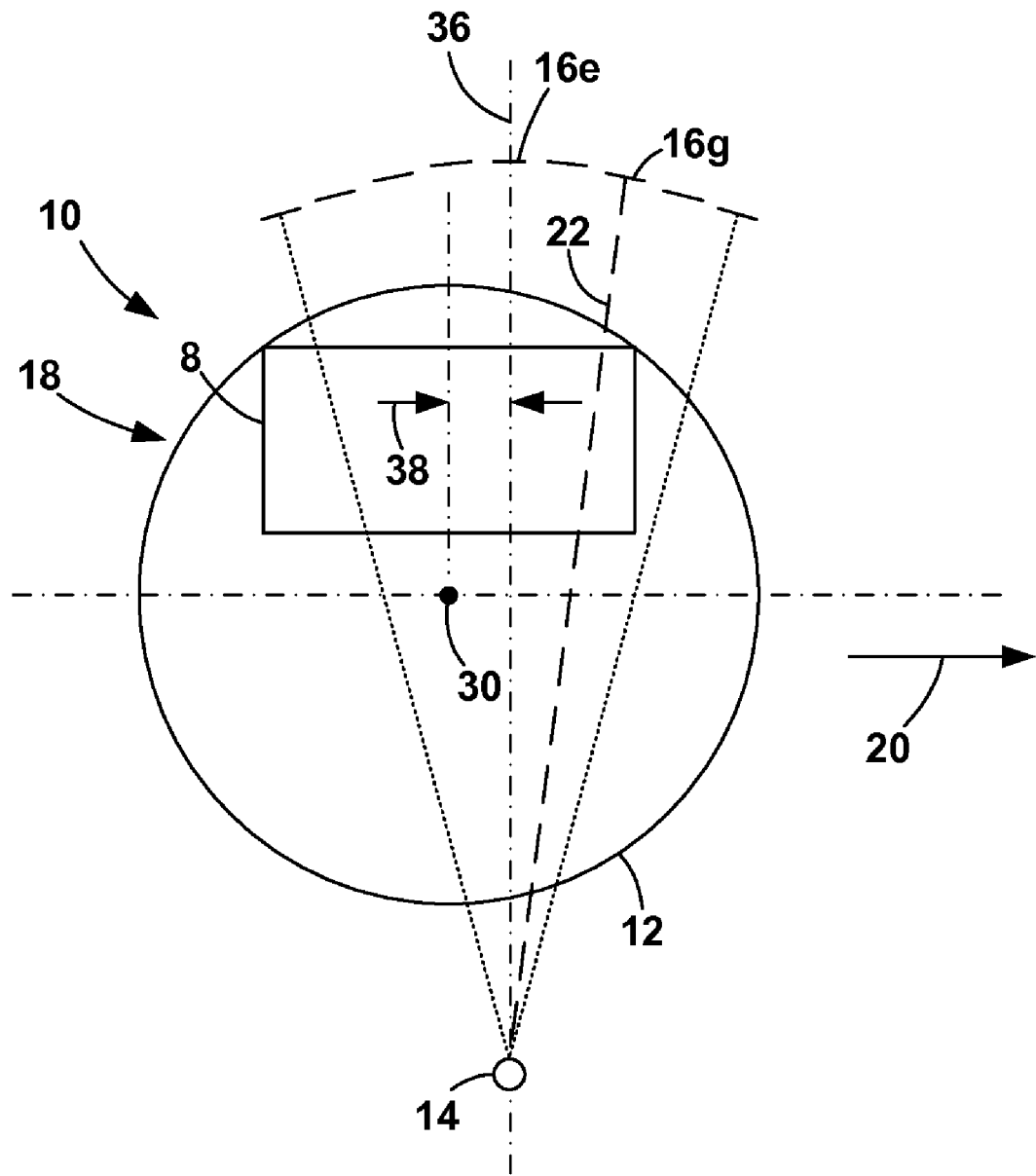
FIG. 4 is a diagram showing an alternate arrangement of the platform relative to the x-ray source and detectors.

There are situations where the inner voxels 32—those nearest to the platform axis 30—will not traverse one or more outer detector columns 16. FIG. 4 shows an alternate configuration of the system that fully or partially alleviates this problem. In this configuration, the rotating platform axis 30 is offset, as at 38, from the system center line 36, the line between the x-ray source 14 and the central detector column 16e. This configuration permits more angular views and, if the displacement is large enough, allows each voxel to traverse every detector column 16, thereby producing the maximum amount of data for each voxel.

In another configuration of the system that fully or partially alleviates the problem with the inner voxels 32, the rotating platform 12 (with the object 8) is translated, as at 20, through the object space 18 in the plane of the platform 12, as in FIGS. 1 and 2. Although it guarantees that every voxel 32 will traverse every detector column 16 during translation, it complicates the calculations for determining which detector elements 34 are to be sampled. At each instant of time during the process, the position of every voxel 32 relative to the x-ray source 14 and every detector column 16 is known by measuring the rotation angle of the platform 12 and the position of platform 12 in translation.

The following is a mathematical description of the process of the present invention. As described above, each voxel 32 is sampled a number of times from different angles in order to produce data to calculate an image. This procedure determines which detector element 34 in a detector column 16 is sampled to obtain data for a given voxel 32 at a given rotation angle. The procedure assumes that the platform axis 30 is stationary relative to the x-ray source 14 and detector columns 16 and that the platform axis 30 is aligned between the x-ray source 14 and the center detector column.

Figure 5:
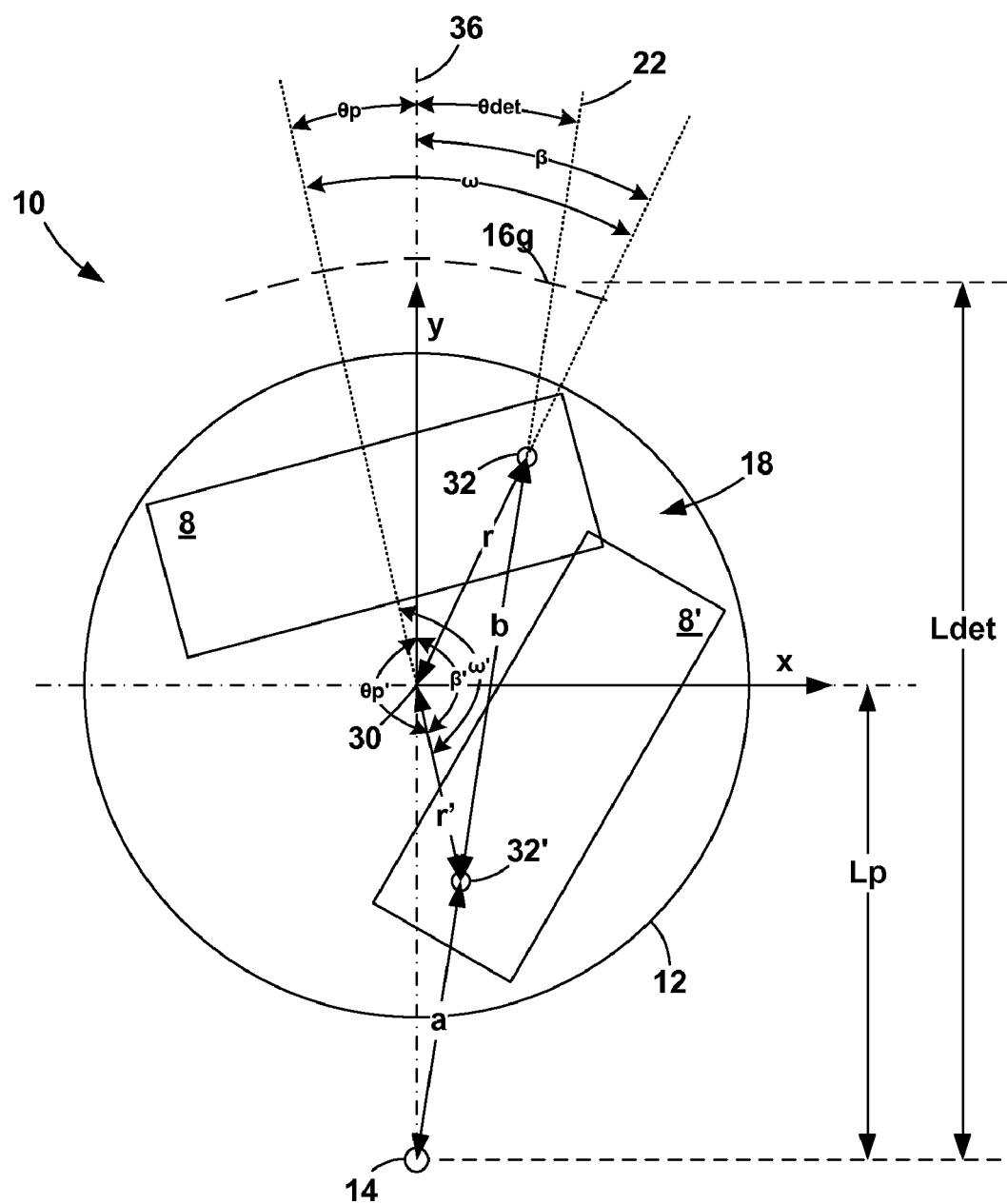
FIG. 5 is a top view showing the coordinate system and variables for calculating images.
Figure 6:
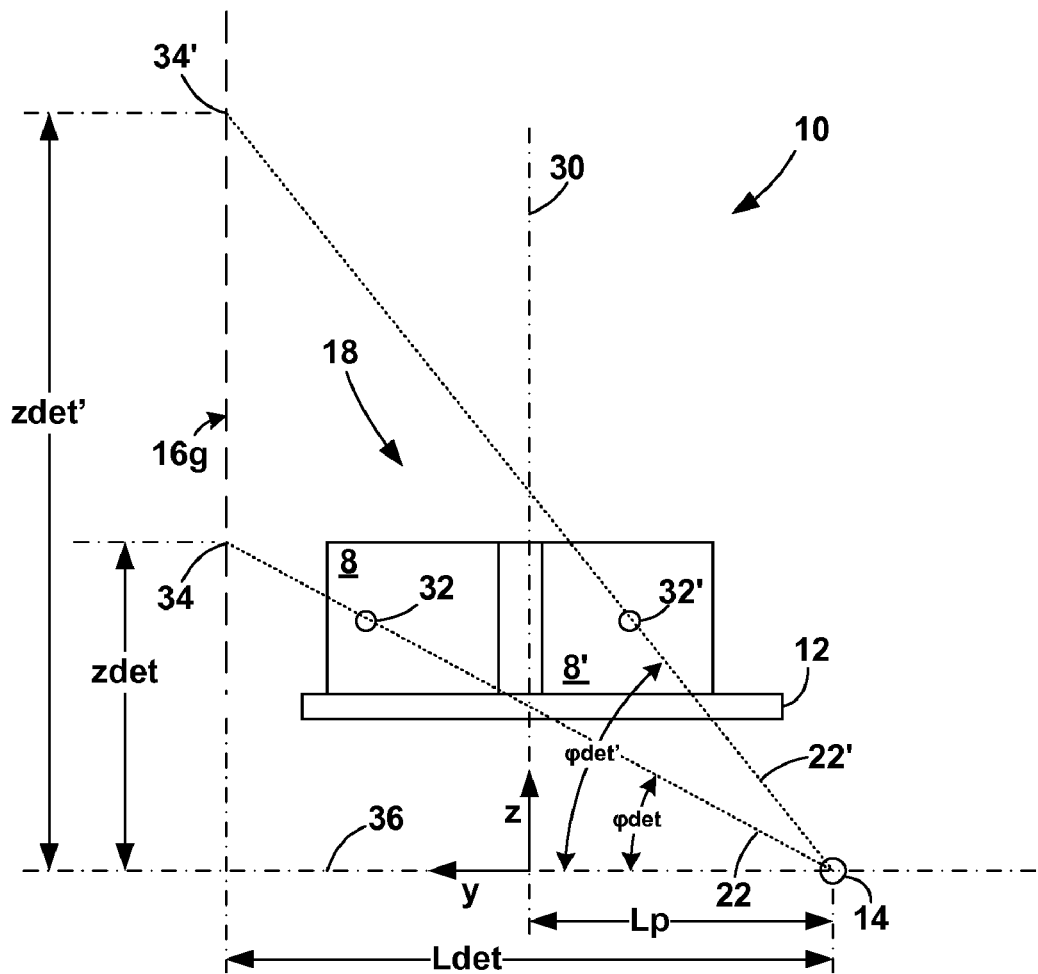
FIG. 6 is a side view showing the coordinate system and variables for calculating images.

A voxel 32, 32' within the object 8, 8' is denoted by the coordinates (x,y,z). The apostrophe (prime) indicates the parameters associated with the second view of the voxel. For example, the object 8 is the object when it is in position for the first view of the voxel and object 8' is the object when it is in position for the second view of the voxel. The origin (x=0, y=0, z=0) is on the platform axis 30 in the horizontal plane of the x-ray source 14 parallel to the platform 12. In FIG. 5, x is horizontal, y is vertical, and z is perpendicular to the sheet. In FIG. 6, x is perpendicular to the page, y is horizontal, and z is vertical.

θdet is the angle in the XY plane between the fixed center line 36 of the system (in the YZ plane where x=0) and the detector column 16g that the x-ray beam 22 that intersects the voxel 32 impinges upon. zdet is the height of the detector element 34 to sample in the detector column 16g defined by θdet. φdet is the angle between the XY plane where z=0 and the x-ray beam 22 that intersects the voxel 32. zdet' and φdet' are the corresponding values of zdet and φdet for the second view of the voxel 32' that uses the same detector column θdet. Ldet is the horizontal distance from the x-ray source 14 to the detector column 16g with the detector element 34 to sample. Lp is the horizontal distance from the x-ray source 14 to the platform axis 30.

The procedure uses the following example numerical parameters, which are merely illustrative and not intended to be limiting. The location (x,y,z) of the voxel 34 is x=17.94 cm, y=22.14 cm, and z=40 cm. θdet=8.97°=0.157 rad, Ldet=107.36 cm, and Lp=55.98 cm.

Using FIG. 5 and well known geometrical formulas, $r=\sqrt{(x^2+y^2)}$, $\omega=a\tan(x/y)$, and $\sin(\theta det)=0.156$. Again from FIG. 5, $\beta=\theta det+a\sin((Lp/r)*\sin(\theta det))=0.468$ radians. $\theta p=\omega-\beta$, $\theta p=0.213$ radians or $\theta p*180/\pi=12.212°$. Similarly, $\beta'=\theta det+\pi-a\sin((Lp/r)*\sin(\theta det))=2.987$ radians. $\theta p'=\omega-\beta'=-2.306$ radians and $\theta p*180/\pi=-132.116°$. $\pi-\beta'=0.155$ radians and $0.163*180/\pi=9.339°$.

Using FIGS. 4 and 5, $a=r((\sin(\beta')/\sin(\theta det))$ and $b=r((\sin(\beta'-\beta)/\sin(\beta-\theta det))$. The values of zdet and zdet' corresponding to (x,y,z) are $zdet=z(Ldet/(a+b))$ and $zdet'=z(Ldet/a)$. So the values of φdet and φdet' corresponding to (x,y,z) are $\phi det=a\tan(z(Ldet/((a+b)^2)))$ and $\phi det'=a\tan(z(Ldet/a2))$. The final values of the zdet to be sampled are zdet=52.103 cm and zdet'=152.451 cm and the final values of the φdet to be sampled are $\phi det*180/\pi=32.299°$ and $\phi det'*180/\pi=79.531°$.

This algorithm assumes that the detector columns are vertical (parallel to the platform axis). However, as seen in FIGS. 1 and 3, many actual systems use L-shaped detectors for compactness. In order to determine the correct detector element on the horizontal portion of the detector column, the calculated vertical location on the detector column is projected onto the horizontal portion of the detector column using simple trigonometric calculations.

As mentioned above, the described calculations assume that the platform axis 30 is stationary relative to the x-ray source 14 and detector columns 16. In the configuration of FIG. 4, where the platform axis 30 is offset from the center of the system, the calculations must be adjusted for that offset. In the configuration of FIGS. 1 and 2, where the platform 12 translates between the x-ray source 14 and the detector columns 16, the calculations must be adjusted for the continuous motion of the object 8 in the x direction.

Once all of the data for all of the voxels is acquired, it is used with any appropriate laminography algorithm to produce images of the object.

One application of the present invention is the inspection of airplane carryon bags. The largest allowable dimension for a carryon bag is about 65 cm×45 cm×30 cm (about 26"×18"×12").

The centrifugal acceleration of a carryon bag of this size is calculated, in units of the gravitational constant (g), in order to determine if the bag will stay on the platform as it rotates during inspection and stand up to the g loading. The maximum dimension of the bag from the center of the rotating platform, R, is the radius of the platform, In the present example R=45 cm (0.45 m). The centrifugal acceleration is $R\omega^2$, where $\omega=2*\pi*f$ and f is the rotation frequency. Assuming that the inspection time, i.e., the time for a single rotation of the platform, is 5 seconds—this time may be made shorter or longer as desired—the frequency of rotation of the bag is 0.2 revolutions/s. Thus, the maximum number of g's at the farthest point of the bag from the center of rotation is $0.45*(2*\pi*0.2)^2/9.81=0.07$ g. This is much less than the g loading that the bag receives in ordinary handling and requires only a minimum amount of retaining force to hold the bag on the platform while it rotates. For example, the friction between the bag and a roughened rotating platform is likely sufficient to keep the bag from sliding on the platform during rotation.

Another application of the present invention is to the inspection of shipping pallets, which are about 4' long×4' wide×3' high. The system is modified relative to the carryon bag application as follows:

1. Since the x-rays must penetrate the diagonal of the pallet as it is rotated and this diagonal with a 4'×4'×3' pallet is approximately 5.7°, the x-ray energy must be increased from the usual energy for a carryon bag inspection system of 160 KeV to at least 1 MeV.

2. The distance between the x-ray source and the line of detectors (Ldet in the figures) is approximately 13' and the height of the horizontal arm of the L-shaped detector columns is greater than 4'.

3. The rotating platform has a diameter of about 6'.

4. The thickness of the detector elements is increased appropriately to efficiently detect the more penetrating x-rays.

Thus it has been shown and described a method of producing a laminography image which satisfies the objects set forth above.

Since certain changes may be made in the present disclosure without departing from the scope of the present invention, it is intended that all matter described in the foregoing specification and shown in the accompanying drawings be interpreted as illustrative and not in a limiting sense.

What is claimed is:

1. A method for producing a laminography image of an object comprising the steps of:
   (a) providing a system comprising (1) an x-ray translucent, rotating platform having a vertical axis of rotation, a radius, and a top surface with an object space adapted to receive said object; (2) an x-ray source below said platform surface and horizontally spaced from said axis; and (3) a plurality of vertical columns of x-ray detector elements, a center line extending from said x-ray source to one of said detector columns, said columns being spaced from each other horizontally and generally perpendicularly to said center line, said columns being spaced horizontally from said axis generally opposite said platform from said x-ray source;

(b) for each voxel in said object space: (1) choosing a detector column; (2) determining when said voxel is aligned between said x-ray source and said chosen detector column; (3) determining a first detector element of said chosen detector column on a line extending from said x-ray source to said voxel; (4) sampling said first detector element as first data; (5) rotating said platform until said voxel is next aligned between said x-ray source and said chosen detector column; (6) determining a second detector element of said chosen detector column on a line extending from said x-ray source to said voxel; and (7) sampling said second detector element as second data;

(c) performing step (b) for each detector column; and (d) employing said first data and said second data from each voxel in each detector column in a laminography algorithm.

2. The method of claim 1 wherein said data for all voxels is acquired during one 360° rotation of said platform.

3. The method of claim 1 wherein said platform axis is offset horizontally and perpendicularly to said center line.

4. The method of claim 1 wherein said platform translates horizontally and perpendicularly to said center line between said x-ray source and said detector columns.

5. The method of claim 1 wherein said detector columns are arranged in a small arc about said x-ray source.

6. The method of claim 1 wherein said x-ray source is spaced from said platform axis by a distance at least that of said platform radius.

* * * * *